United States Patent

Bönigk et al.

[11] Patent Number: 5,140,852
[45] Date of Patent: Aug. 25, 1992

[54] PROCESS AND APPARATUS FOR MEASURING THE DEGREE OF FILAMENT INTERMINGLING OF A MULTIFILAMENT YARN

[75] Inventors: Burkhard Bönigk, Königsbrunn; Ingolf Jacob, Untermeitingen; Peter Kretschmer, Bobingen; August Schneider, Grossaitingen, all of Fed. Rep. of Germany

[73] Assignee: Hoechst Aktiengeellschaft, Fed. Rep. of Germany

[21] Appl. No.: 714,665

[22] Filed: Jun. 13, 1991

[30] Foreign Application Priority Data

Jun. 15, 1990 [DE] Fed. Rep. of Germany ....... 4019106

[51] Int. Cl.⁵ ............................................. G01N 21/86
[52] U.S. Cl. ................................. 73/160; 73/159; 356/429; 356/238; 250/559; 250/571
[58] Field of Search ............ 73/160, 159; 250/559, 250/571; 356/429, 238

[56] References Cited

U.S. PATENT DOCUMENTS

| | | | |
|---|---|---|---|
| 3,016,743 | 1/1962 | Promislow et al. | 73/160 |
| 3,273,328 | 9/1966 | Bloch | 57/351 |
| 3,290,932 | 12/1966 | Hitt | 73/160 |
| 3,401,559 | 9/1968 | Rice | 73/160 |
| 3,669,552 | 6/1972 | Briscoe | 356/238 |
| 3,793,883 | 2/1974 | Goldfarb et al. | 73/160 |
| 4,165,638 | 8/1979 | Verlin | 73/160 |
| 4,213,056 | 7/1980 | Matsumura et al. | 73/160 |
| 4,634,280 | 1/1987 | Paulson, Jr. | 250/571 |
| 4,719,576 | 1/1988 | Sano et al. | 73/160 |
| 4,990,793 | 2/1991 | Bonigk et al. | 250/571 |

FOREIGN PATENT DOCUMENTS

| | | | |
|---|---|---|---|
| 0951402 | 7/1974 | Canada | 73/160 |
| 0707102 | 5/1941 | Fed. Rep. of Germany | 73/160 |
| 0561799 | 10/1923 | France | 73/160 |
| 1137386 | 1/1985 | U.S.S.R. | 73/160 |

OTHER PUBLICATIONS

"Interlace Measuring Instrument," Research Disclosure, No. 156, p. 18 (Apr. 1977).

Primary Examiner—William A. Cuchlinski, Jr.
Assistant Examiner—Diego F. F. Gutierrez
Attorney, Agent, or Firm—Connolly & Hutz

[57] ABSTRACT

There are described a process and apparatus for measuring the degree of filament intermingling of an intermingled multifilament yarn. The intermingled yarn is moved through a self-conveying fluid jet (air jet). The yarn substantially fills out the jet channel and emerges from the jet in a virtually tensionless state. Owing to the pressure difference at the jet outlet, noncohesive yarn zones expand explosively in the manner of a balloon. After expansion, the yarn passes before a sensor means, preferably an electronic camera, which detects the lightness differences or light diffraction phenomena due to the yarn filaments and sends as a function thereof a signal to a signal processing means. The method of measurement of the invention makes it possible to obtain very accurate information about the nature of the intermingling (spot type or continuous) and also about the geometry of intermingling (for example number and spacing of intermingling nodes in the case of spot type intermingling).

23 Claims, 2 Drawing Sheets

PROCESS AND APPARATUS FOR MEASURING THE DEGREE OF FILAMENT INTERMINGLING OF A MULTIFILAMENT YARN

BACKGROUND OF THE INVENTION

The invention relates to a process and apparatus for measuring the degree of filament intermingling of an intermingled multifilament yarn, which can be a single- or multi-component yarn.

The methods of measurement used in the field, such as the pin count test and the Interlace Counter, are increasingly proving unsatisfactory, given the standard reached today in intermingling. For instance, the pin count test no longer provides meaningful information at a very high entanglement density and fails completely in the case of continuous intermingling.

DE Offenlegungsschrift 2,839,439 discloses a process and apparatus for measuring the degree of filament intermingled of an intermingled multifilament yarn wherein open zones of the intermingled yarn are expanded and sensed in contactless fashion. To expand the yarn, the yarn is in this case guided over a vaulted transparent plate, and changes in the yarn are detected by means of a photodetector arrangement. This method of measurement permits only batchwise operation. In EP 340 600 the yarn to be monitored is placed on an aspirated conveyor belt and then likewise sensed b means of an optical sensor. The disadvantage with both prior art processes is that, during measurement, the yarn is in contact with mechanical parts and deformed by that contact, which can lead to a corresponding distortion of the measured signal.

SUMMARY OF THE INVENTION

It is an object of the present invention to provide a process and apparatus for measuring the degree of filament intermingling of an intermingled multifilament yarn which permit as accurate and comprehensive a characterization of the degree of filament intermingling of the yarn as possible.

To achieve this object, the process of the present invention and the apparatus of the present invention are defined by the following features. According to the present invention, the open zones of the yarn are expanded using a stream of fluid, in particular an air stream. The expanding and also the contactless sensing take place in a zone in which the yarn is surrounded exclusively by fluid, in particular air. In contradistinction to the prior art discussed at the beginning, the yarn is thus not in contact with any mechanical parts in the measuring zone. Therefore, the yarn is free to expand in all directions, subject of course to any constraint due to the yarn itself.

To expand the yarn, it is preferably passed through a fluid jet. The fluid jet can be an air-operated interlacing jet as described for example in U.S. Pat. No. 3,273,328, where it is used for interlacing one or more yarn components. In contradistinction to this prior art, the process of the present invention provides that the yarn passes out of the fluid jet in an essentially tensionless state, so that the noncohesive zones of the yarn expand explosively in balloon fashion at the jet exit. To make the fluid jet self-conveying, the yarn should be subjected in the fluid jet to a stream of fluid (air stream) which has a component of movement which extends in the direction of the jet axis.

The "controlled explosion" which takes place at the jet exit thus serves to "blow open" the open (i.e. nonintermingled) yarn zones and any lightly coalesced and-/or stuck-together yarn zones in balloon fashion. This reveals the degree of filament intermingling (coherency) of the yarn to a particular degree. which permits precise monitoring of the degree of filament intermingling. Since, furthermore, the expanded yarn is not in contact with any mechanical parts, there is no possibility of the measured signal being distorted by an otherwise unavoidable deformation of the yarn. The invention makes possible not only an accurate, but also a comprehensive, characterization of the degree of filament intermingling. For instance, the invention makes it possible to ascertain whether any intermingling is of the spot type or of the continuous type. It is also possible to ascertain the degree of intermingling of two or more yarn components ("single- or multi- plaited" coherency). In the case of spot type intermingling it is possible to determine missing entanglements, the number of entanglements per yarn length, and the average lengths of the intermingled and nonintermingled yarn zones.

Furthermore, the invention makes it possible to obtain information about the yarn coherency force.

As mentioned earlier, the yarn should not be pulled out of the fluid jet under tension but, as it were, should be forced out of the self-conveying fluid jet. The "controlled yarn explosion" at the jet outlet is all the more marked the higher the pressure drop on exit. To this end, the yarn should be moved through the fluid jet at a sufficiently high fill level that the yarn fills out the jet channel virtually completely. This also prevents renewed intermingling of the yarn within the fluid jet. The sensing of the expanded yarn can be effected optically or by means of ultrasound. The preferred proposal is that the yarn be monitored in the expanded area by an electric camera, preferably a line camera.

Preferably, a light source or a laser is arranged on the camera remote side of the yarn for illuminating the yarn. The diode row provided in the line camera detects the lightness differences or diffraction phenomena due to the yarn filaments in its measuring field. The resulting measured signal is transmitted to a signal processing means which includes for example a controller which digitizes the analog signal and sends it to an arithmetic processing unit for evaluation.

Since the method of measurement employed in the present invention is contactless and therefore independent of forces of inertia, it is possible to obtain extremely high speeds of examination. This dramatically improves the reliability of the data. For instance, the process of the present invention makes it possible to examine several 100 m of yarn within a period within which only 30 cm or 5 m respectively can be examined in the pin count test or with the Interlace Counter.

Moreover, the invention makes it possible to measure the yarn on-line, which is not possible with the prior art processes.

In a further aspect of the invention it is provided that to measure the yarn in three dimensions the sensing takes place in two mutually orthogonal directions. This can be done for example using two mutually orthogonal electronic cameras.

Furthermore, it is particularly advantageous to conduct the process of the present invention in such a way that a stress is put on the yarn before its entry into the fluid stream. The stressing of the yarn advantageously takes the form for example of subjecting the yarn to an elastic stretch or of deflecting it ground sharp corners. If other aspects are to be examined, the stressing takes the form of a cyclic stress being placed on the yarn. Preferably, to this end, two spaced-apart (in the running direction) controllable conveyor means (e.g. godets) are arranged upstream of the fluid jet, whereby a selectable tension can be imparted to the yarn to be introduced into the fluid jet. This makes it possible to stretch the yarn elastically in order in this way to simulate the stress due to the intermingling on, for example, weaving or knitting machines. By switching the stretching mechanism on and off it is possible to detect the difference between virgin intermingled and elastically stretched yarn in only a single examination. This provides otherwise virtually unattainable information about the yarn coherency force due to the intermingling.

The process of the present invention can also be used with particular advantage for measuring a multicomponent yarn in order to be able to identify and located incompletely intermingled zones of the yarn.

The present invention also provides an apparatus for carrying out the process of the present invention for measuring the degree of filament intermingling of an intermingled multifilament yarn. This apparatus comprises a means for expanding open zones of the intermingled yarn, a sensor means which senses the expanded yarn contactlessly and generates a measurement signal as a function thereof, and a signal processing means for the measurement signal, the means for expanding open zones of the yarn comprising a fluid jet through which the intermingled yarn is guided, and the sensor means is arranged in the area of the jet outlet.

The fluid jet has at least one blasting channel which extends at an angle to the longitudinal direction of the jet and ends in the jet channel, so that the fluid jet is self-conveying.

Downstream of the fluid jet is arranged an adjustable conveyor means which removes the yarn in an essentially tensionless state from the fluid jet.

Preferably, the fluid jet is likewise preceded by two adjustable conveyor means which are spaced apart in the transport direction and which impart a selectable tension to the yarn to be introduced into the fluid jet.

The sensor means preferably comprises an electronic camera, in particular a line camera, which optically senses the yarn in the expanded area. Particular technical advantages are offered by a sensor means which has a second electronic camera whose optical axis is perpendicular to that of the first camera.

Advantageously, a light source or a laser for illuminating the yarn is arranged on the camera remote side of the yarn.

Particular preference is given to an apparatus of the present invention whose signal processing means includes a controller which digitizes the analog signal received from the sensor means and passes it to an arithmetic processing unit for evaluation.

BRIEF DESCRIPTION OF THE DRAWINGS

An illustrative embodiment of the invention will be explained with reference to the drawings, where.

DETAILED DESCRIPTION OF THE INVENTION

Figure 1:
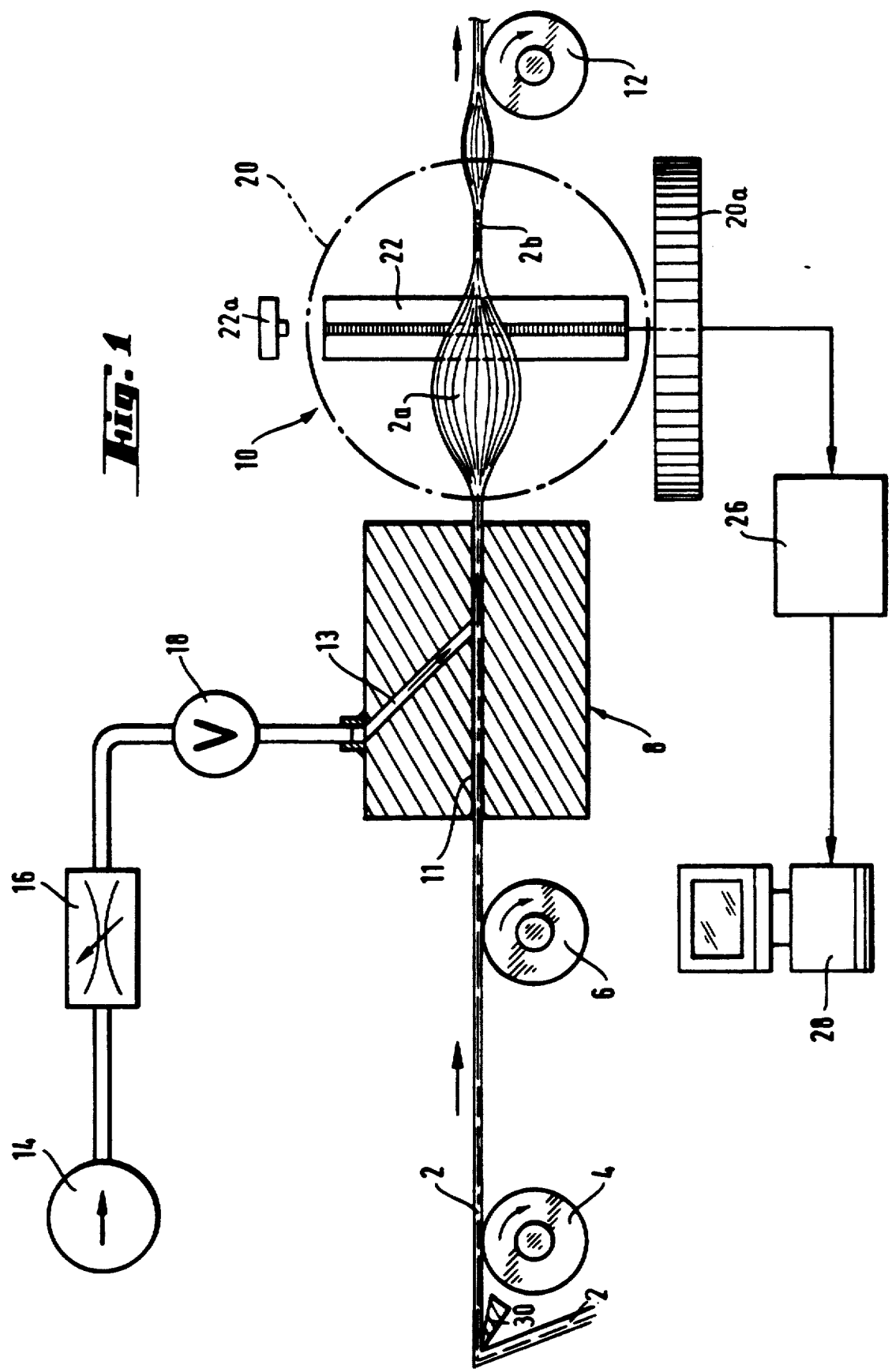
FIG. 1 is a schematic view of an apparatus for measuring the degree of filament intermingling of an intermingled multifilament yarn.

The apparatus shown schematically in FIG. 1 has two conveyor means 4, 6 in the form of a godet system, a fluid jet 8, a sensor means 10 and another godet system conveyor means 12, through which the intermingled multifilament yarn 2 to be examined passes in succession.

The fluid jet 8 is by design an air interlacing jet having a jet channel 11 which receives the yarn 2 and one or more blasting channels 13 which end in the jet channel 11. The blasting channels 13 are supplied with compressed air by a compressed air source 14 via a pressure reducing means 16 and a shut-off valve 18. The blasting channels 13 are arranged at an acute angle (for example 45°) relative to the jet channel 11, so that the blasting air streams into the jet channel 11 with a horizontal component of movement and as a result effects the conveyance of the yarn 2 through the fluid jet 8.

The yarn 2 thus need not be pulled at the jet outlet. The conveyor means 12 only has the purpose to force the otherwise whipping yarn 2 into a uniaxial running direction. The speed of the conveyor means 12 is regulated here via a weighing cell (not depicted) in such a way that the tension on the yarn 2 on exit from the jet is virtually zero.

The diameter of the yarn 2 and the diameter of the jet channel 11 are chosen in such a way that the yarn 2 fills out the jet channel 11 virtually completely. This prevents a further intermingling of the yarn 2. It also produces a particularly marked pressure drop at the jet outlet.

Owing to this pressure drop the yarn 2, which in the depicted illustrated embodiment is a spot-intermingled yarn having open zones 2a and cohesive zones 2b, expands explosively in the manner of a balloon—shown schematically—at the jet outlet.

In the area in which the expanding air opens out the open zones 2a is arranged the sensor means 10 which comprises a light source 20 and an electronic camera 22 in the form of a line camera. The light source 20 and the line camera 22 are arranged on mutually opposite sides of the yarn 2 and the diode strip of the line camera 22 detects the lightness differences between the areas which transmit the light and the areas obscured by the filaments of the yarn 2.

The power of resolution of the line camera 22 should be such that it can detect the individual filaments of a yarn of very fine denier (for example 0.5 dtex). The length of the diode row of the line camera 22 is for example 26 mm, over which distance 2048 image-resolving elements are arranged in a row. The spacing between successive pairs of these elements is 13 $\mu$m. The minimum exposure time is 500 $\mu$s.

The line camera 22 generates an analog signal which is passed to a controller 26. The controller 26, which is equipped with an A/D converter, digitizes the signal and passes it to a high-speed arithmetic processing unit 28. The arithmetic processing unit 28 then evaluates the signal, which can also be depicted visually on a screen. To be able to detect the degree of filament intermingling of the yarn 2 in three dimensions it is possible to provide additionally to the sensor means 10 a second sensor means at an angle of 90°. Such three-dimensional monitoring of the yarn would be important in particular in the case of yarns or yarn zones which are not rotationally symmetrical. The conveyor means 4, 6 arranged upstream of the fluid jet 8 are adjustable in speed, so that they can be used to stretch the yarn 2 elastically. In this way it is possible to simulate the stress on the intermingled yarn to which it will be later exposed on a weaving or knitting machine. Moreover, in just a single pass it is possible—by switching the stretching on and off—to determine the difference between tensionless and elastically stretched yarn, which makes it possible to provide information about the yarn coherency force.

Figure 2:
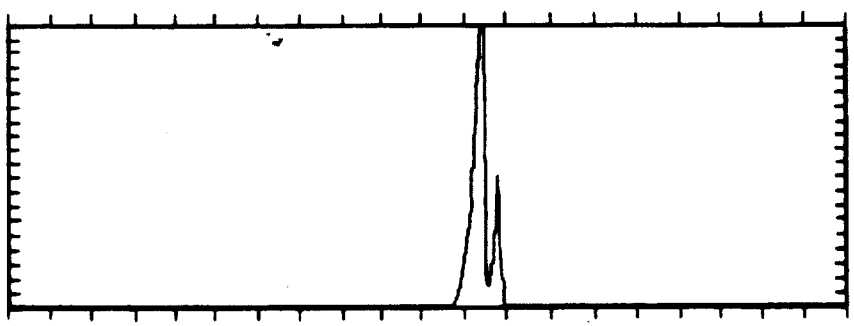
FIGS. 2 to 5 are diagrams which depict examples of the signal generated by the apparatus of FIG. 1.
Figure 3:
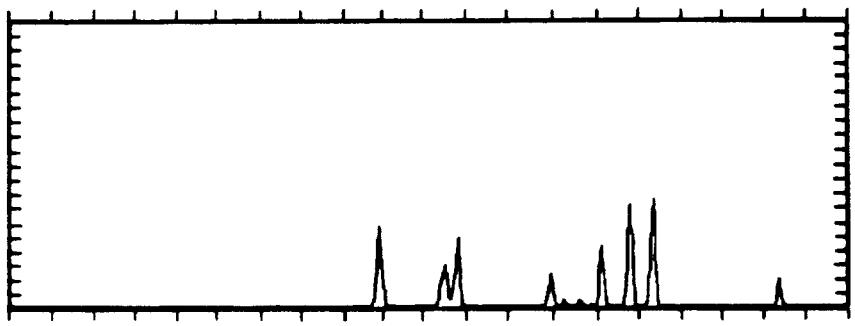

The apparatus shown in FIG. 1 makes it possible to detect the open and cohesive zones 2a, b of a spot-intermingled multifilament yarn 2 at high speed. For instance, the signal shown in the diagram of FIG. 2 represents a cohesive zone of a spot-intermingled 50-dtex 40-filament yarn, while the diagram of FIG. 3 represents an open zone of the same yarn.

Figure 4:
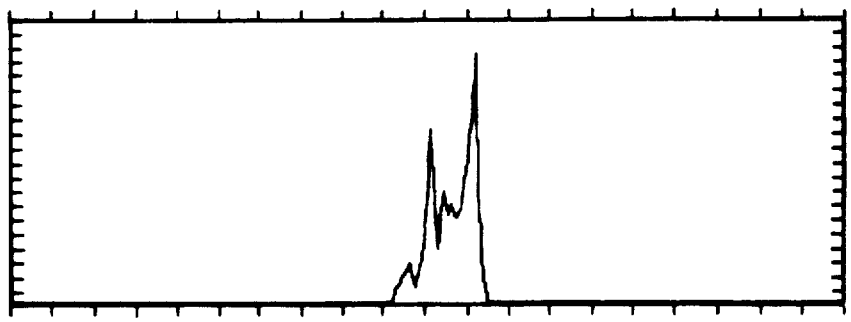
Figure 5:
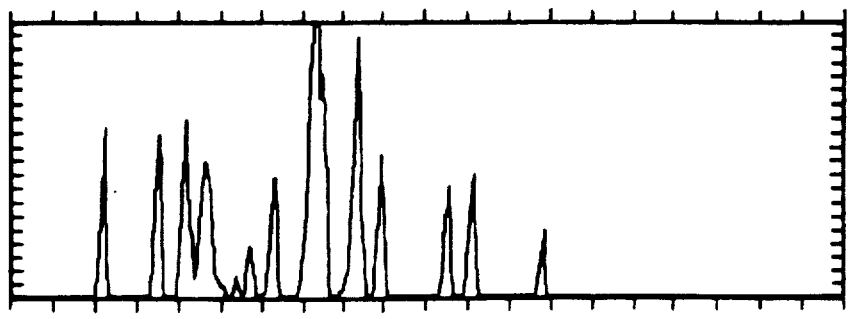

The apparatus of FIG. 1 can be used to examine textured yarns as well as smooth yarns. The signal shown in FIG. 4 represents a cohesive textured 50-dtex 40-filament yarn, while the signal of FIG. 5 applies to a nonintermingled opened smooth 50-dtex 40-filament yarn. The examination with the apparatus of FIG. 1 can take place on-line. At a speed of 800 m/min 6.7 mm of yarn would cross the diode row of the line camera per 500 μs. A stroboscope or rotating slotted disk (not shown) can shorten this exposure time still further.

FIG. 1 also illustrates a second light source 20a and a second line camera 22a which are in orthogonal position to the light source 20 and line camera 22. When the second light source and second camera are used the yarn is measured in three dimensions. Additionally, FIG. 1 illustrates an altered yarn path where the yarn is deflected around a sharp object 30.

What is claimed is:

1. A process for measuring the degree of filament intermingling of an intermingled multifilament yarn where open zones of the intermingled yarn are expanded and sensed contactlessly, which comprises effecting the expanded with a fluid stream, performing the expanding in an area in which the yarn is surrounded exclusively by a fluid contactlessly sensing the expanded yarn in the area in which the yarn is surrounded exclusively by the fluid, and producing a signal representative of the degree of filament intermingling.

2. The process of claim 1, wherein the intermingled yarn is moved through a fluid jet and passed out of the fluid jet in an essentially tensionless state, so that the open yarn zones expand instantaneously at the jet outlet.

3. The process of claim 2, wherein the yarn is subjected in the fluid jet to a fluid stream which has a component of movement which extends in the direction of the jet axis.

4. The process of claim 2, wherein the yarn is moved through the fluid jet at a sufficiently high fill level that the yarn fills out the jet channel virtually completely.

5. The process of claim 1, wherein the sensing is effected optically.

6. The process of claim 5, wherein the yarn is illuminated in the expanded area and the lightness differences which arise there are detected by an electronic camera, preferably a line camera.

7. The process of claim 5, wherein the yarn is irradiated in the expanded area with a laser and the light diffraction phenomena which arise there are detected by an electronic camera, preferably a line camera.

8. The process of claim 1, wherein to measure the yarn in three dimensions the sensing takes place in two mutually orthogonal directions.

9. The process of claim 1, wherein the yarn is stressed before entry into the fluid stream.

10. The process of claim 9, wherein the stressing takes the form of elastic stretching of the yarn.

11. The process of claim 9, wherein the stressing takes the form of deflecting around sharp corners.

12. The process of claim 9, wherein the stressing takes the form of cyclic stressing.

13. The process of claim 9, wherein during a single pass a selectable stress is switched on and off to determine the difference between virgin intermingled yarn and stressed intermingled yarn in order to obtain information about the yarn coherency force due to the intermingling.

14. The process of claim 1, for measuring a multicomponent yarn in order to be able to identify and locate incompletely intermingled zones of the yarn.

15. The process of claim 1, carried out in an on-line operation.

16. Apparatus for measuring the degree of filament intermingling of an intermingled multifilament yarn, comprising a means for expanding open zones of the intermingled yarn, a sensor means which senses the expanded yarn contactlessly and generates a signal as a function thereof, and a signal processing means for the signal, wherein the means for expanding the open zones of the yarn comprises a fluid jet (8) through which the intermingled yarn (2) passes and the sensor means (10) is arranged in the area of the jet outlet.

17. Apparatus of claim 16, wherein the fluid jet (8) has a jet channel (11) and at least one blasting channel (13) which extends at an angle to the longitudinal direction of the jet channel and which ends in the jet channel (11), so that the fluid jet (8) is self-conveying.

18. Apparatus of claim 16, wherein the fluid jet (8) is followed on the downstream side by an adjustable conveyor means (12) which removes the yarn (2) from the fluid jet (8) in an essentially tensionless state.

19. Apparatus of claim 16, wherein the fluid jet (8) is preceded in the upstream direction by two adjustable conveyor means (4, 6) which are spaced apart in the transport direction and which confer a selectable tension to the yarn (2) to be introduced into the fluid jet (8).

20. Apparatus of claim 16, wherein the sensor means (10) comprises an electronic camera, in particular a line camera (22), which senses the yarn (2) optically in the expanded area.

21. Apparatus of claim 20, wherein a light source (20) or a laser for illuminating the yarn (2) is arranged on the side of the yarn (2) opposite the camera (22).

22. Apparatus of claim 20, wherein the sensor means has a second electronic camera whose optical axis is perpendicular to that of the first camera.

23. Apparatus of claim 16, wherein the signal processing means has a controller (26) which digitizes the analog signal received from the sensor means (10) and passes it to an arithmetic processing unit (28) for evaluation.

* * * * *